US00PP19587P3

(12) United States Plant Patent
Meilland

(10) Patent No.: US PP19,587 P3
(45) Date of Patent: Dec. 23, 2008

(54) SHRUB ROSE PLANT NAMED 'MEIROSCLEM'

(50) Latin Name: *Rosa hybrida*
Varietal Denomination: cv. Meirosclem

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/586,714

(22) Filed: Oct. 26, 2006

(65) Prior Publication Data

US 2008/0134372 P1 Jun. 5, 2008

(51) Int. Cl.
*A01H 5/00* (2006.01)

(52) U.S. Cl. ..... Plt./102
(58) Field of Classification Search ..... Plt./102
See application file for complete search history.

(56) References Cited

U.S. PATENT DOCUMENTS

| | | | | |
|---|---|---|---|---|
| PP3,351 | P | * | 6/1973 | McGredy, IV |
| PP4,224 | P | * | 3/1978 | Buck |
| PP5,956 | P | * | 4/1987 | Meilland |
| PP15,740 | P2 | * | 4/2005 | Lim et al. |
| 2008/0134372 | P1 | * | 6/2008 | Meilland |

* cited by examiner

*Primary Examiner*—Wendy C. Haas
(74) *Attorney, Agent, or Firm*—Buchanan Ingersoll & Rooney PC

(57) ABSTRACT

A new and distinct variety of shrub rose plant is provided which forms in abundance on a substantially continuous basis attractive single blossoms that are salmon-orange in coloration and are dusted with red picotee coloration. A compact and mounding growth habit with vigorous vegetation is displayed. Attractive satiny ornamental green foliage is formed that contrasts nicely with the blossom coloration. Superior resistance to Black Spot is exhibited The new variety is particularly well suited for growing as ornamentation in the landscape.

1 Drawing Sheet

Figure 1:
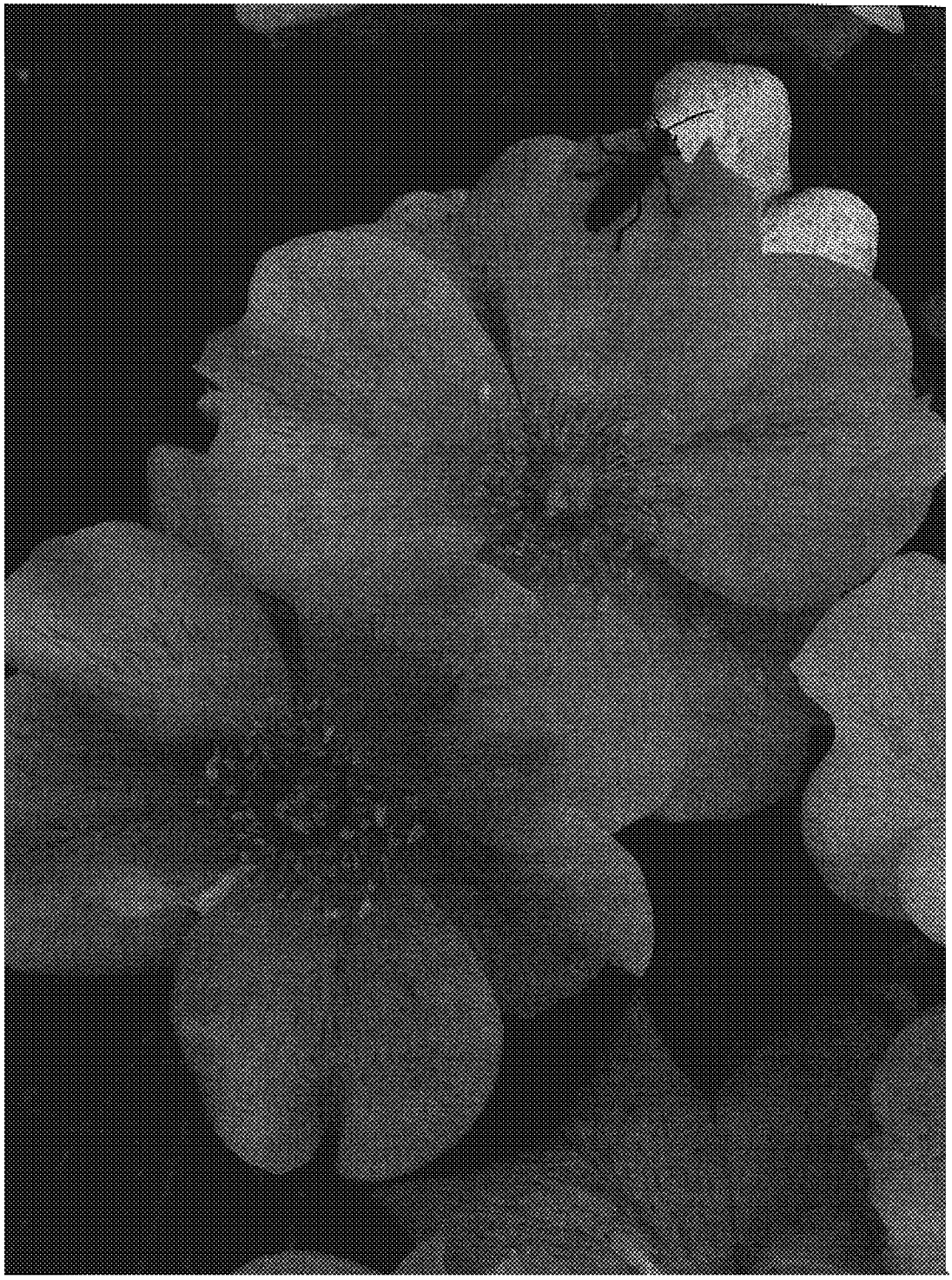

Botanical/commercial classification: *Rosa hybrida*/Shrub Rose Plant.
Varietal denomination: cv. Meirosclem.

SUMMARY OF THE INVENTION

The new variety of *Rosa hybrida* shrub rose plant of the present invention was created by artificial pollination wherein two parents were crossed which previously had been studied in the hope that they would contribute the desired characteristics. The female parent (i.e., the seed parent) was the product of the cross of the 'Bucbi' variety (U.S. Plant Pat. No. 4,225) and the 'Macpic' variety (U.S. Plant Pat. No. 3,351). The male parent (i.e., the pollen parent) of the new variety was the product of the cross of the 'Meipoque' variety (U.S. Plant Pat. No. 5,956) and the 'Applejack' variety (non-patented in the United States). The parentage of the new variety can be summarized as follows:

'('Bucbi'×Macpic')×('Meipoque'×'Applejack').

The seeds resulting from the above pollination were sown and small plants were obtained which were physically and biologically different from each other. Selective study resulted in the identification of a single plant of the new variety. The distinctive characteristics of the new variety have been further confirmed while growing at Wasco, Calif., U.S.A.

It was found that the new shrub rose plant of the present invention possesses the following combination of characteristics:

(a) abundantly forms on a substantially continuous basis attractive single blossoms that are salmon-orange in coloration and are dusted with red picotee coloration,
(b) exhibits a compact and mounding growth habit,
(c) forms vigorous vegetation,
(d) forms attractive ornamental green foliage with a satiny finish,
(e) exhibits superior resistance to Black Spot, and
(f) is particularly well suited for providing attractive ornamentation in the landscape.

The attractive salmon-orange blossoms contrast nicely with the satiny green foliage.

The new variety well meets the needs of the horticultural industry. It can be grown to advantage as ornamentation in parks, gardens, public areas, and in residential settings.

The new variety of the present invention also can be readily distinguished from its ancestors. More specifically, the 'Bucbi' variety is a considerably larger plant and forms blossoms that are light rose in coloration having more petals. The 'Macpic' variety forms deep pink semi-double blossoms having lighter edges and a white eye. The 'Meipoque' variety also is considerably larger plant and forms deep pink blossoms having a white eye. The 'Applejack' variety forms large semi-double neyron rose blossoms that are strippled with crimson coloration.

The characteristics of the new variety have been found at Waso, Calif., U.S.A., and near West Grove, Pa., U.S.A., to be homogeneous and stable and to be strictly transmissible by asexual propagation such as budding, grafting, and the rooting of cuttings from one generation to another. The new variety reproduces true to type by such asexual propagation.

The new variety has been named 'Meirosclem', and is being marketed under the IMPOSTER trademark.

BRIEF DESCRIPTION OF THE PHOTOGRAPH

The accompanying photograph shows, as nearly true as it is reasonably possible to make the same in a color illustration of this character, a typical flowering plant of the new variety. The illustrated rose plant of the new variety was approximately two years of age and was observed during September while growing outdoors on 'Dr. Huey' (unpatented) rootstock near West Grove, Pa., U.S.A.

The photograph shows the typical salmon-orange blossoms that are dusted with spots of red picotee coloration.

DETAILED DESCRIPTION

The chart used in the identification of colors is that of the Royal Horticultural Society (R.H.S. Colour Chart, Third Edition, 1995), London, England. The description is based on the observation of two-year-old specimens of the new variety during September while growing outdoors on 'Dr. Huey' rootstock near West Grove, Pa., U.S.A.

Class: Landscape Shrub.

Plant:

*Height.*—Approximately 45 to 60 cm on average at the end of the growing season.

*Width.*—Approximately 45 to 60 cm on average at the end of the growing season.

*Habit.*—Compact, mounding, and bushy.

Branches:

*Thorns.*—Size: approximately 5 mm in length on average. Configuration: substantially triangular when viewed from the side. Frequency: long prickles≧4 mm commonly number approximately 9 on average on adult stems and approximately 1 on average on young stems, and small prickles ≦4 mm commonly number approximately 11 on average on adult stems and approximately 10 on average on young stems. Base: somewhat oval, approximately 4 mm in length on average, and approximately 2 mm in width on average. Color: near Brown Group 200D on mature wood.

*Nodes.*—Internode length: approximately 1.9 cm on average. Diameter: approximately 0.5 cm on average. Color: near Greyed-Purple Group 184A.

Leaves:

*Length.*—For a three-leaflet leaf approximately 48 mm on average, and for a five-leaflet leaf approximately 62 mm on average.

*Width.*—For a three-leaflet leaf and a five-leaflet leaf approximately 60 mm on average at the widest point.

*Leaflets.*—Number 3, 5 and rarely 7. Arrangement: alternate and pinnate. Shape: typically ovate with a rounded base, and an acuminate tip. Size: commonly approximately 40 mm in length on average and approximately 28 mm in width on average. Margins: fine serrulate. Texture: smooth. Overall appearance: very dense, leathery, and medium green with a satiny finish. Color (young foliage): Upper surface: near Yellow-Green Group 144B with highlights of Red-Purple Group 59A at the margins. Color (adult foliage): Upper surface: commonly Green Group 136B to Yellow-Green Group 147B.

*Petioles.*—Length: approximately 25 mm on average. Diameter: approximately 1 mm on average. Texture; glabrous. Color: near Yellow-Green Group 145A.

*Rachis.*—Length: approximately 35 mm on average. Diameter: approximately 1 mm on average. Texture: glabrous. Color: near Yellow-Green Group 145A.

*Stipules.*—Length: approximately 10 mm on average. Width: approximately 2.5 mm on average. Texture: glabrous. Color: near Yellow-Green Group 145A.

Inflorescence:

*Number of flowers.*—Commonly one bloom per stem.

*Peduncle.*—Approximately 40 mm in length on average, approximately 1.5 mm in diameter on average, typically covered with small spines, and Yellow-Green Group 144B in coloration.

*Sepals.*—Typically five in number, possess an acuminate tip and a truncate base, approximately 24 to 27 mm in length on average, approximately 5 to 6 mm in width on average, the upper surface commonly is covered with fine white hairs, the under surface commonly is covered with short rigid projections, and with a few foliaceous extensions at the edges.

*Buds.*—Shape: ovate. Length: approximately 15 to 20 mm on average as the calyx breaks. Width: approximately 7 to 10 mm on average as the calyx breaks. Texture: scabrous with a short hard point. Color: near Yellow-Green Group 145A prior to the opening of the sepals.

*Flower.*—Form: single and informal. Shape: flat when fully open. Diameter: approximately 60 to 70 mm on average when fully open. Color when blooming: Upper surface: mainly Red Group 47D with random darker picotee areas of near Red Group 53B, and Yellow Group 3A at the base. Under surface: mainly Red Group 47B with random picotee areas of near Red Group 49B, and Yellow Group 3A at the base. Fragrance: faint. Petal shape: wedge-shaped with a curled apex. Petal number: commonly approximately 5 on average under normal growing conditions. Petal texture: glabrous. Petal margin: entire Petal apex: rounded. Petal base: commonly cuneate to narrowly cuneate. Petal size: commonly approximately 35 to 40 mm in length on average, and approximately 30 to 35 mm in width on average. Petal drop: very good with the petals detaching cleanly and freely before drying. Stamen number: approximately 75 on average. Anthers: commonly approximately 1.8 to 2 mm in length on average, approximately 1 mm in width on average, and near Yellow-Orange Group 33A in coloration. Filaments: typically approximately 9 to 12 mm in length, approximately 1 mm in diameter, and near Red Group 48B in coloration. Pollen: near Yellow-Orange Group 22A in coloration. Styles: approximately 4.2 mm in length on average, and near Orange-Red Group 33A in coloration. Stigmas: commonly approximately 0.6 mm in length, approximately 1 mm in width, and near Yellow-Orange Group 19B in coloration with some patches of Orange Group 29B. Receptacle: when flowers are fully open commonly approximately 8 mm in length and approximately 5 mm in diameter. Lasting quality: commonly approximately one week on the plant as well as when cut and placed in a vase.

Development:

*Vegetation.*—Vigorous and strong.

*Blossoming.*—Abundant and substantially continuous.

*Resistance to diseases.*—Superior with respect to Black Spot.

*Formation of hips/seeds.*—None observed during observations to date.

I claim:

1. A new and distinct shrub rose plant characterized by the following combination of characteristics:

(a) abundantly forms on a substantially continuous basis attractive single blossoms that are salmon-orange in coloration and are dusted with red picotee coloration, (b) exhibits a compact and mounding growth habit, (c) forms vigorous vegetation, (d) forms attractive ornamental green foliage with a satiny finish, (e) exhibits superior resistance to Black Spot, and (f) is particularly well suited for providing attractive ornamentation in the landscape;

substantially as herein shown and described.

* * * * *